United States Patent [19]

Clark

[11] 4,389,531
[45] Jun. 21, 1983

[54] PREPARATION OF N-SUBSTITUTED ANILINES

[75] Inventor: Gary T. Clark, Kingsport, Tenn.

[73] Assignee: Eastman Kodak Company, Rochester, N.Y.

[21] Appl. No.: 350,936

[22] Filed: Feb. 22, 1982

Related U.S. Application Data

[63] Continuation-in-part of Ser. No. 158,748, Jun. 12, 1980, abandoned, which is a continuation of Ser. No. 26,481, Apr. 2, 1979, abandoned.

[51] Int. Cl.$^3$ .............................................. C07C 67/30
[52] U.S. Cl. ...................................................... 560/43
[58] Field of Search ......................................... 560/43

[56] References Cited

U.S. PATENT DOCUMENTS

| Re. 29,468 | 11/1977 | Clayton | 560/43 |
| 2,470,094 | 5/1949 | Dickey et al. | 560/43 |
| 3,978,064 | 8/1976 | Johnson et al. | 560/43 |
| 4,013,662 | 3/1977 | Harbert | 560/43 X |

OTHER PUBLICATIONS

Wagner et al., Synthetic Org. Chem. (1965), pp. 654–657.
Glickman et al., Jour. Amer. Chem. Soc., vol. 67 (1945), pp. 1017–1020.

*Primary Examiner*—Bernard Helfin
*Attorney, Agent, or Firm*—Donald W. Spurrell; Daniel B. Reece, III

[57] ABSTRACT

Disclosed is a process for the preparation of disperse dye couplers of the general formula

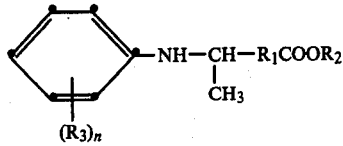

wherein $R_1$, $R_2$ and $R_3$ are typical groups such as straight or branched alkylene for $R_1$, phenyl, cyclohexyl or straight or branched substituted or unsubstituted alkyl for $R_2$, hydrogen, lower alkyl, halogen, lower alkoxy, acylamido and the like for $R_3$, and n is 1, 2 or 3, comprising contacting under hydrogen atmosphere a mixture of at least one amine compound of the formula

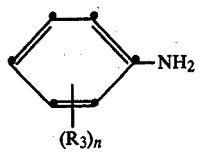

or its nitro precursor and at least one compound of the formula

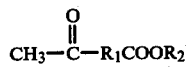

in the presence of from about 1 to about 10 parts of a hydrogenation catalyst per part of the amine or its nitro precursor, and from about $5.3 \times 10^{-4}$ to about $1.0 \times 10^{-1}$ mole per mole of said amine or its nitro precursor of one or more of lower alkyl sulfonic acid or benzenesulfonic acid which may be substituted with 1–3 lower alkyl groups such as p-toluenesulfonic acid.

4 Claims, No Drawings

PREPARATION OF N-SUBSTITUTED ANILINES

This is a continuation-in-part application of Ser. No. 158,748, filed June 12, 1980, which is a continuation of Ser. No. 26,481, filed Apr. 2, 1979 both now abandoned.

This invention concerns certain reduction reactions and specifically reductive alkylations of aromatic amines or their nitro precursors employing carbonyl compounds and hydrogenation catalyst.

In the reductive alkylation of many aromatic amines and their nitro precursors employing typical hydrogenation catalysts such as platinum and palladium in the presence of e.g., acids such as acetic, the yield of alkylated amine is very low or essentially non-existent, and the product is often not readily isolatable from the reaction system.

An object therefore of the present invention is to provide an improved reductive alkylation process for obtaining improved yields of alkylated amines which have heretofore been difficult to obtain.

This and other objects hereinafter appearing have been attained in accordance with the present invention through the discovery that hydrogenation catalysts such as platinum in the presence of one or more of lower alkyl sulfonic acids such as methane and ethane sulfonic acids, benzene sulfonic acid, and naphthalene sulfonic acid, each of which may be substituted with 1-3 lower alkyl groups, particularly p-toluenesulfonic acid (PTSA) greatly improves the yield and purity of a large number of alkylated amine products prepared by reductive alkylation.

The improved process is particularly useful in the preparation of disperse dye couplers of the general formula

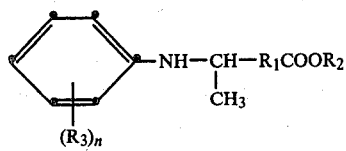

wherein $R_1$ is selected from straight or branched alkylene of 1-4 carbons, $R_2$ is selected from phenyl, cyclohexyl and straight or branched alkyl of 1-10 carbons which may be substituted with lower alkoxy, lower alkoxyalkoxy, benzyl, or cyclohexyl, and $R_3$ is selected from hydrogen, lower alkyl, lower alkoxy, lower alkanoylamino, and aryl, and n is 1, 2 or 3. The term "lower" as used herein means 1-6 carbons.

As aforesaid, these couplers may be prepared from the aromatic amine or its nitro precursor and the ketone as typified by the following preparation of 3-(2'-methoxy-5'-acetamidoanilino)butyrate.

EXAMPLE 1

A mixture of 105.0 g. (0.5 mole) of 2-nitro-4-acetamidoanisole, 67.0 g. (0.5 mole) of ethyl acetoacetate, 550 ml. of isopropyl alcohol, 10.0 g. of 5% Pt/C, and 3.0 g. of p-toluenesulfonic acid is treated in an autoclave at 165° C. and 1,000 psi of hydrogen until the uptake of hydrogen ceases. The solvent and catalysts are removed. Upon standing, 143.8 g. (98%) of ethyl 3-(2'-methoxy-5-acetamidoanilino)butyrate is obtained. NMR analysis of the product supports the proposed structure.

Using the procedure of Example 1, the couplers listed below were obtained in good yield. For some of these preparations denatured ethanol was used in place of isopropanol.

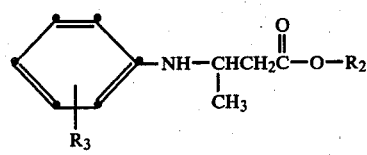

| $R_3$ | $R_2$ |
|---|---|
| 3-HNCOCH$_3$ | C$_2$H$_5$ |
| 2-CH$_3$; 5-NHCOCH$_3$ | C$_2$H$_5$ |
| 3-HNCOCH$_3$ | C$_2$H$_4$OCH$_3$ |
| 3-HNCOCH$_3$ | C$_6$H$_{11}$ |
| 3-HNCOCH$_3$ | C$_4$H$_9$ |
| 3-HNCOCH$_3$ | CH$_2$C$_6$H$_5$ |
| 2-OCH$_3$; 5-HNCOCH$_3$ | C$_4$H$_9$ |
| 2-OCH$_3$; 5-HNCOCH$_3$ | CH$_2$C$_6$H$_5$ |
| 2-OCH$_3$; 5-HNCOCH$_3$ | C$_2$H$_4$OC$_2$H$_4$OC$_2$H$_5$ |
| 2-OCH$_3$; 5-HNCOCH$_3$ | CH$_2$—CHC$_4$H$_9$<br>\|<br>C$_2$H$_5$ |
| 2-OCH$_3$; 5-HNCOCH$_3$ | —CH(CH$_3$)$_2$ |
| 3-CH$_3$ | C$_2$H$_5$ |
| 2-CH$_3$ | C$_2$H$_5$ |
| 2-OCH$_3$ | C$_2$H$_5$ |
| 2-OCH$_3$; 5-CH$_3$ | C$_2$H$_5$ |
| 2-OCH$_3$; 5-OCH$_3$ | C$_2$H$_5$ |

The ketones useful in the present invention are prepared for example from diketene and the appropriate alcohol according to the general procedure given organic Synthesis, 42, 28 (1962), John Wiley & Sons, Inc., N.Y. A typical preparation is as follows:

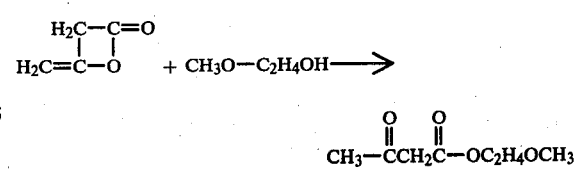

The following preparations were made in order to compare yields using the present PTSA and prior art co-catalysts or promotors, using approximately the same number of moles of each and the same amount of 5% Pt/C catalyst.

EXAMPLE 2

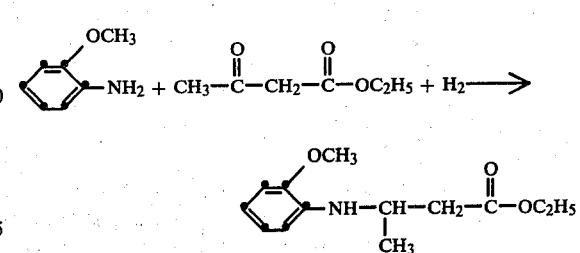

93.84% yield using PTSA 62% yield using HOAC

EXAMPLE 3

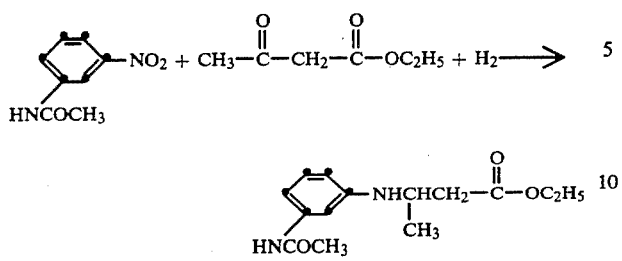

32% yield with HOAC vs. 74% yield with PTSA

EXAMPLE 4

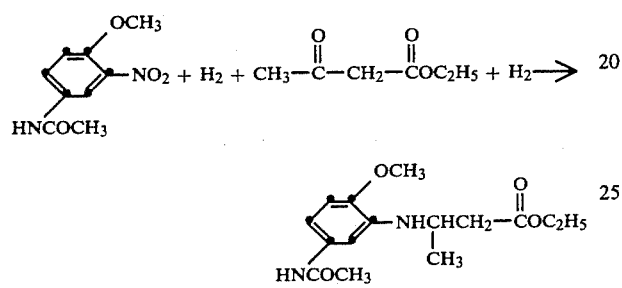

39% yield with HOAC vs. 96.7% yield with PTSA

EXAMPLE 5

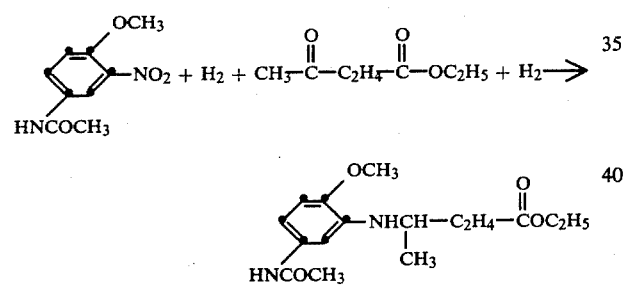

0.0 yield with HOAC vs. 83% yield with PTSA

The above examples demonstrate the extraordinary efficiency of the present process in which the PTSA may be used in concentrations of from about $5.3 \times 10^{-4}$ to about $1 \times 10^{-1}$ moles per mole of the amine or its nitro precursor, preferably from about $1.3 \times 10^{-3}$ to about $8.5 \times 10^{-2}$ moles. The catalyst may be any of the known hydrogenation catalysts such as platinum black, collodial platinum, platinum oxide as a precursor, 5% platinum on carbon, Raney nickel (e.g., sodium hydroxide leached 1:1, nickel:aluminum alloy), rhenium oxide e.g. trioxide, ruthenium as the metal or dioxide, copper chromite, palladium on CaCO$_3$ or charcoal or other known carriers including BaSO$_4$, rhodium, and mixtures thereof, with the 5% platinum on carbon, Pt/c, being preferred. The catalyst may be used e.g. in concentrations of from about 0.1 to about 20 parts by weight per part of the amine or its precursor, with from about 1 to about 10 parts being preferred. The hydrogenation temperature is between about 75 and about 200° C., preferably 150° and 165° C., and the hydrogen pressure may be, for example, between about 100 and about 2000 psi at the start of the autoclave reaction, preferably between about 500 and about 3000 psi with from about 1000 to about 1500 psi being most preferred.

The preferred embodiment of the present process is defined as the process for preparing compounds of the formula

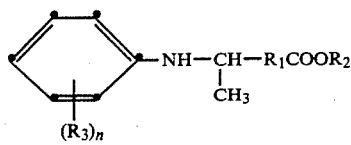

wherein R$_1$ is selected from straight or branched alkylene of 1-4 carbons, R$_2$ is selected from phenyl, cyclohexyl and straight or branched alkyl of 1-10 carbons which may be substituted with lower alkoxy, lower alkoxyalkoxy, benzyl, or cyclohexyl, and R$_3$ is selected from hydrogen, lower alkyl, lower alkoxy, lower alkanoylamino, and aryl, and n is 1, 2 or 3, comprising contacting at between about 75° C. and 200° C. under hydrogen at between about 100 and 3,000 psi, a mixture of at least one compound of the formula

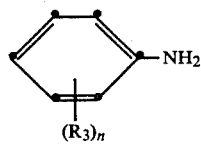

or its nitro precursor and at least one compound of the formula

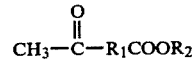

in the presence of from about 0.1 to about 30 parts of a hydrogenation catalyst per part of the amine or its nitro precursor, and from about $5.3 \times 10^{-4}$ to about $1.0 \times 10^{-1}$, preferably from about $1.3 \times 10^{-3}$ to about $8.15 \times 10^{-2}$ moles per mole of said amine or its nitro precursor of one or more of lower alkyl sulfonic acid, p-toluene sulfonic acid, benzenesulfonic acid, or naphthalene sulfonic acid, each of which may be substituted with 1-3 lower alkyl groups. The most preferred process employs p-toluene sulfonic acid and a platinum catalyst. It is noted that the hydrogenation catalyst contains typically from about 1.0% to about 5.0% of the metal i.e., Pt, Ni, etc., on support material such that the actual amount of catalytic metal is but a small fraction of the catalyst weight.

The following table lists a number of reactant combinations which further illustrate but do not limit the present invention.

| R$_1$ | R$_2$ | R$_3$ |
|---|---|---|
| —C$_2$H$_4$— | —C$_2$H$_5$ | H |
| " | " | 2-CH$_3$ |
| " | " | 2-OCH$_3$ |
| " | " | 2,5-di-CH$_3$ |
| " | " | 2,5-di-OCH$_3$ |
| " | " | 2-CH$_3$, 5-OCH$_3$ |
| " | " | 2-OCH$_3$, 5-CH$_3$ |
| " | " | 2-CH$_3$, 5-NHCOCH$_3$ |
| " | " | 5-NHCOCH$_3$ |
| " | " | 5-NHCOC$_6$H$_5$ |
| —C$_4$H$_8$—n | " | 2-OCH$_3$, 5-NHCOCH$_3$ |

-continued

| $R_1$ | $R_2$ | $R_3$ |
|---|---|---|
| " | " | 5-Cl |
| " | " | 2,5-di-NHCOCH$_3$ |
| —C$_2$H$_4$ | " | 2-CH$_3$ |
| " | C$_6$H$_5$ | " |
| " | C$_6$H$_{11}$ | 2-OCH$_3$ |
| " | —CH$_2$C$_6$H$_5$ | " |
| " | —C$_2$H$_4$OC$_2$H$_5$ | 2,5-di-CH$_3$ |
| " | —C$_2$H$_4$OC$_2$H$_4$OC$_2$H$_5$ | 2,5-di-OCH$_3$ |
| " | —C$_2$H$_4$OCOCH$_3$ | 5-Cl |
| " | —C$_2$H$_4$NHCOCH$_3$ | 5-NHCOCH$_3$ |
| " | —C$_2$H$_4$Cl | 2-CH$_3$, 5-OCH$_3$ |
| —C$_3$H$_6$—n | —C$_2$H$_4$OH | 5-NHCOC$_6$H$_5$ |
| " | —CH$_2$C$_6$H$_{11}$ | 2,5-di-CH$_3$ |
| " | " | 5-Br |

The invention has been described in detail with particular reference to preferred embodiments thereof, but it will be understood that variations and modifications can be effected within the spirit and scope of the invention.

I claim:

1. The process for the preparation of disperse dye couplers of the general formula

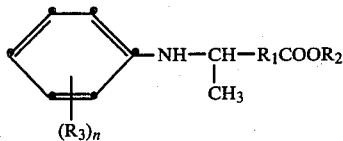

wherein R$_1$ is selected from straight or branched alkylene of 1-4 carbons, R$_2$ is selected from phenyl, cyclohexyl and straight or branched alkyl of 1-10 carbons which may be substituted with lower alkoxy, lower alkoxyalkoxy, benzyl, or cyclohexyl, and R$_3$ is selected from hydrogen, lower alkyl, lower alkoxy, lower alkanoylamino, and aryl, and n is 1, 2 or 3, comprising contacting at between about 75° C. and 200° C. under hydrogen at between about 100 and 3,000 psi a mixture of at least one amine compound of the formula

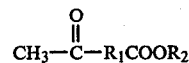

or its nitro precursor and at least one compound of the formula $$CH_3-\overset{O}{\underset{\|}{C}}-R_1COOR_2$$

in the presence of from about 0.1 to about 30 parts by weight of a hydrogenation catalyst per part by weight of the amine or its nitro precursor, and from about $5.3 \times 10^{-4}$ to about $1.0 \times 10^{-1}$ moles per mole of said amine or its nitro precursor of one or more of lower alkyl sulfonic acid, p-toluenesulfonic acid, benzenesulfonic acid, or naphthalene sulfonic acid, each of which may be substituted with 1-3 lower alkyl groups.

2. The process of claim 1 wherein the hydrogenation catalyst is platinum on carbon.

3. The process of claim 1 wherein the reactants are selected from ethyl acetoacetate and a compound selected from

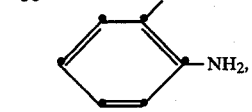 

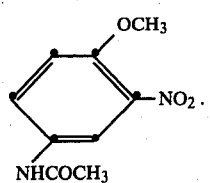

4. The process of claim 1 wherein the sulfonic acid is p-toluenesulfonic acid in a concentration of from about $1.3 \times 10^{-3}$ to about $8.15 \times 10^{-2}$ moles per mole of said amine compound or its nitro precursor.

* * * * *